United States Patent [19]

van de Kooi

[11] 4,049,012

[45] Sept. 20, 1977

[54] METHOD AND DEVICE FOR MEASURING AND KEEPING CONSTANT THE WATER CONTENT IN A SALT BATH

[75] Inventor: Johannes Maria van de Kooi, Montfoort, Netherlands

[73] Assignee: SKF Industrial Trading and Development Company B.V., Nieuwegein, Netherlands

[21] Appl. No.: 724,917

[22] Filed: Sept. 20, 1976

[30] Foreign Application Priority Data

Sept. 22, 1975 Netherlands .......................... 7511138

[51] Int. Cl.² ............................................. G05D 11/08

[52] U.S. Cl. .......................................... 137/3; 137/88; 137/93

[58] Field of Search ................... 137/3, 88, 93

[56] References Cited

U.S. PATENT DOCUMENTS

| | | | |
|---|---|---|---|
| 3,292,650 | 12/1966 | Bird | 137/93 |
| 3,645,802 | 2/1972 | Keough | 148/15 |

*Primary Examiner*—Robert G. Nilson
*Attorney, Agent, or Firm*—Daniel M. Rosen

[57] ABSTRACT

A method and apparatus for measuring and keeping constant the water content in a highly heated salt bath, by measuring the change in dew point of a gas flowed over the salt bath.

14 Claims, 1 Drawing Figure

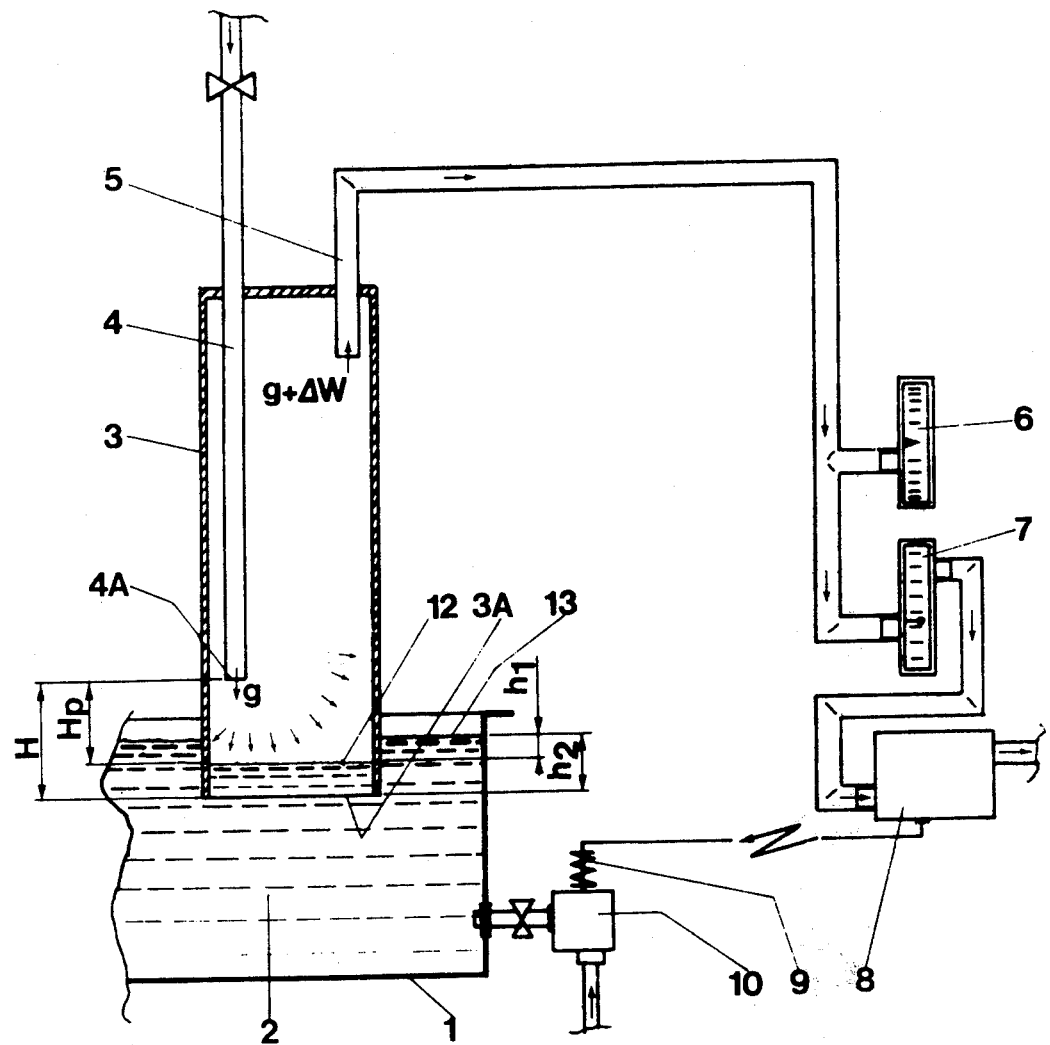

METHOD AND DEVICE FOR MEASURING AND KEEPING CONSTANT THE WATER CONTENT IN A SALT BATH

BACKGROUND OF THE INVENTION

The invention relates to a method for measuring and keeping constant the water content in a highly heated salt bath, where the pressure of the water vapor over the salt bath depends on or corresponds to the quantity of water in the bath, and also to a device for performance of the method.

As is generally known, the quenching or cooling of heat-treated materials during the process of hardening and tempering is often done in a salt bath whose action is greatly influenced, for example, by the chemical composition of the bath, the temperature of the bath, the movement of the salt in the bath itself, the degree of fouling of the bath and also its water content. It has been found in practice that problems are posed in particular by regulation of the water content or proportion in the salt bath.

The present invention relates to an improvement of the quenching or cooling effect, and hence in the hardening and tempering of the materials. This improvement comprises a method and device wherein the water content is continuously measured and kept constant, or at any rate the required percentage or proportion is maintained in the salt bath, with due allowance made for the relatively high temperature. In this connection it can be taken as generally known, that the temperature in such a salt bath may be between 150°-550° C, and moreover that a relatively small loss of water can, for instance, substantially affect the hardness of the metal being hardened and tempered. Tests have shown, in fact, that in the case of bolts made of plain carbon tool steel which are heat-treated at temperatures of 850°-930° C, followed by cooling in a salt bath at a temperature between 180°-200° C, a 0.2 vol % loss of water from the salt bath serves to lower the hardness from 62 HRc to 45 HRc. This shows how very important it is to keep the water content or proportion of water constant in salt baths of this kind.

SUMMARY OF THE INVENTION

The present invention discloses a method together with a device for performing the method, which is not only surprisingly simple in application and execution, but also, as has been proved in practice, quarantees optimum reliable operation. The new method includes introduction of a gas with a certain dew point over a part of the salt bath where it absorbs the water vapor and is then removed via a measuring and control device which measures its dew point. Through the change in the measured dew point after its absorption of the water vapor, with respect to a pre-set value for the dew point of the gas, water or steam is supplied to the salt bath of the supply of same, as applicable. The gas so employed as a carrier gas will absorb a large quantity of water vapor in the event of the vapor pressure over the salt bath being relatively high, and a smaller percentage of water vapor if the vapor pressure is low. The method according to the invention makes judicious use of this phenomenon to influence the water content in the salt bath.

The above-described method differs in principle from a measuring method as is described in the U.S. Pat. No. 3,645,802, which method is based on the fact that the electrical resistance of the salt quench bath varies as a function of the temperature and the amount of water in the bath.

It has been found that regulation of the supply of water to the salt bath, which regulation is related as above-described to the change of dew point of the gas, can be simply effected by means of a device which, according to the invention, comprises a partly closed measuring tube or measuring chamber within which are a gas admission tube and a gas exhaust tube, the open end of the said measuring tube or measuring chamber being immersed in the salt bath, and the opening of the gas admission tube being closer to the salt bath than the opening of the gas exhaust tube. It is of advantage in this invention that at a certain gas pressure the distance between the outlet of the gas admission tube and the level of the salt bath in the measuring tube is equal to a fixed distance measured between the gas tube opening and the measuring tube opening, less the height difference obtained by reducing the height between the level of the salt bath outside the measuring tube and the measuring tube opening, by the difference in height between the levels of the salt bath respectively outside and inside the measuring tube. It is preferable here that at the gas pressure prevailing, the measuring tube should be immersed in the salt bath to such a depth that the difference between the height measured from the salt bath level outside the measuring tube to the rim of the measuring tube opening, and the height measured between the levels of the salt bath outside and inside the measuring tube shall have a positive value.

The invention will now be described in more detail with reference to the drawing which schematically illustrates a device wherewith the method can be practiced.

BRIEF DESCRIPTION OF THE DRAWING

The single FIGURE is a schematic drawing shown as an elevation view partially in section.

DETAILED DESCRIPTION OF THE PREFERRED EMBODIMENT

The new device or apparatus comprises a tank 1 which contains a salt bath 2, such as a mixture of 50% $KNO_3$ and 50% $NaNO_2$. The temperature of the salt bath is here about 200° C. Partly immersed in the salt bath is a measuring tube 3 containing a gas admission tube 4 and a gas exhaust tube 5. To ensure efficient operation of the device, bearing in mind that a certain gas pressure exists within the measuring tube 3, this measuring tube must be placed at a specific depth in the salt bath 2, which position will be discussed in detail later on in this description.

The gas admission tube 4 is connected to a gas bottle or supply (not shown), and the gas exhaust tube 5 is connected to a gas pressure gauge 6, a gas flowmeter 7 and a dew point meter 8. The meter 8 by means of which the dew point values of the gas are thus continuously recorded, also includes a differential circuit that controls the operation of an electrically operable regulating valve 9 for a steam or water supply system 10 feeding the salt bath tank 1. Thus, with the aid of the device schematically illustrated, it is established that the gas flowing out of the tube 4 and along the salt bath surface 12 shall follow a flowpath where it absorbs water vapor $(g+\Delta W)$. This water vapor-absorbing gas $(g+\Delta W)$ is then passed to the meters 6, 7 and the dew point meter 8 by means of which any variation in dew point from the dew point value required at a certain temperature of the salt bath, causes a signal to be sent to the solenoid valve 9 regulating the water or steam supply and discharge system 10, so as to allow water to flow into the salt bath until the desired dew point value is again attained. Valve 9 is likewise closed automatically by the dew point meter 8.

Of great importance in this process is the immersion depth of the measuring tube 3 in the salt bath 2. It must be realized that the gas g does not, during measurement, flow through the salt bath, but streams above and along the salt bath surface 12 and in so doing absorbs the water vapor. Due to the gas pressure $p$ in the measuring tube 3 there arises between the salt bath surface 12 in the measuring tube 3 and salt bath surface 13 in tank 1, a height difference $h_1$ whose value is equal to the ratio between the gas pressure $p$ and the specific gravity $\rho$ of the salt, viz:

$$h_1 = p \text{ N/cm}^2 / \rho \text{ N/cm}^1$$

The value of $p$ is read off from the meter 6 in the system. Tests have shown that the above condition for efficient operation of the device is satisfied if the distance Hp of the outlet 4A of the admission tube 4 from the salt bath surface 12 in the tube 3, is equal to the fixed distance H between the respective openings 4A and 3A of the gas admission tube 4 and the measuring tube 3, less the difference in height $h_2 - h_1$ of the salt bath, that is, $Hp = H - (h_2 - h_1)$. Here, the height $h_2$ is the height difference between the level 13 of the salt bath outside the measuring tube 3 and the measuring tube opening 3A, while the height $h_1$ indicates the difference between the salt bath levels 13 and 12 respectivey outside and inside the measuring tube 3. Good results were obtained in tests using nitrogen with a dew point below −40° C, the temperature of the salt bath being about 200° C, height $h_1$ equal to 5 cm and height $h_2$ equal to 6-7 cm.

Other examples, modifications, alterations, omissions or additions, will be apparent to those skilled in the art as being within the spirit and scope of the present invention.

What is claimed is:

1. A method for measuring and keeping substantially constant the proportion of water in a salt bath, where the water vapor pressure over the bath corresponds to the proportion of water in the bath, comprising the steps: flowing a gas having a predetermined initial dew point toward and onto the surface of said salt bath, absorbing a quantity of water vapor from said salt bath with said gas and thereby changing the value of said dew point, measuring said change in value of the dew point, and supplying a selected quantity of water to said salt bath for returning the dew point of said bath back to the initial value thereof and thereby maintaining the water proportion of said bath.

2. A method according to claim 1, wherein said bath is in a tank, the method comprising the further steps of partially submerging into the top surface of said salt bath the open end of a container, introducing said gas into said container and toward said surface of the bath, and subsequently exhausting said gas from said container for measuring any change in dew point of said gas due to absorption of water vapor.

3. A method according to claim 2, wherein said salt bath has a top surface designated inner top surface within said container and outer top surface within said tank and external of said container, comprising the further step of maintaining said gas in said container under sufficient pressure to cause said inner top surface to be lower than said outer top surface by a height difference, $h_1$.

4. A method according to claim 3, comprising the further steps of maintaining substantially constant the pressure and temperature of said gas within said container at least during the absorption of water vapor by the gas from the salt bath, said pressure being proportional to the ratio of said height difference, $h_1$, to the specific gravity of said salt bath.

5. A method according to claim 2, comprising the further step of maintaining the temperature of said salt bath in the range of 150° to 550° C.

6. A method according to claim 5, wherein said salt bath comprises a mixture of 50% $KNO_3$ and 50% $NaNO_2$.

7. A method according to claim 5, wherein said gas comprises nitrogen.

8. A device for measuring and maintaining substantially constant the proportion of water in a salt bath in a tank, where the water vapor pressure over the salt bath corresponds to the proportion of water in the bath, comprising: container means for enclosing a space above a portion of the top surface of said salt bath, whereby said surface is designated inner top surface within said container means and outer top surface external of said container means, gas admission means for directing gas with an initial dew point of predetermined value into said space toward and onto said inner top surface with water vapor from said salt bath being absorbed by said gas and the dew point thereof being changed proportionately, gas exhaust means for removing said gas and absorbed water vapor from said space, measuring means for measuring the change in value of the dew point of said removed gas, and control means for adding a quantity of water or steam to said salt bath sufficient to return the dew point thereof to said initial value.

9. A device according to claim 8, wherein said container means comprises a tube having one open end facing downward and partially submerged in said salt bath.

10. A device according to claim 9, wherein said container means is formed by at least one wall, said gas admission means comprises a gas admission tube extending through said wall and having an outlet end spaced a first distance, Hp, from said inner top surface, and said gas exhaust means comprises a tube extending through said wall and having an inlet end spaced a second distance greater than Hp from said inner top surface.

11. A device according to claim 9, further comprising means for maintaining said gas within said space under a pressure such that said inner top surface of the salt bath is at a lower level than said outer top surface by a height, $h_1$, and said container means open end is submerged below said outer top surface to a depth, $h_2$, with $h_2$ being greater in value than $h_1$.

12. A device according to claim 10, comprising means for maintaining said gas within said container at a pressure, p, such that said distance, Hp, is equal to a fixed distance $H - (h_2 - h_1)$, where $H$ = the distance between the gas admission tube outlet end and the container means open end, $h_2$ = the depth of said container means outlet end below said outer top surface, and $h_1$ = the height difference between said inner and outer top surfaces.

13. A device according to claim 8, where said measuring and control means comprise a gas pressure gauge, a gas flow meter and a dew point meter connected in sequence, with gas directed thereto from said gas exhaust means.

14. A device according to claim 8, wherein said salt bath comprises a mixture of 50% KNO$_3$ and 50% NaNO$_2$ maintained at a temperature in the range of 150° to 550° C.

* * * * *

UNITED STATES PATENT AND TRADEMARK OFFICE
CERTIFICATE OF CORRECTION

PATENT NO. : 4,049,012
DATED : September 20, 1977
INVENTOR(S) : Johannes Maria van de Kooi It is certified that error appears in the above-identified patent and that said Letters Patent are hereby corrected as shown below:

Column 3, line 20 change "$cm^1$" to --$cm^3$--.

Signed and Sealed this

Sixteenth Day of May 1978

[SEAL]

Attest:

RUTH C. MASON
Attesting Officer

LUTRELLE F. PARKER
Acting Commissioner of Patents and Trademarks